(12) United States Patent
Ndeithi

(10) Patent No.: US 11,045,096 B2
(45) Date of Patent: Jun. 29, 2021

(54) FINGER BLOOD MONITOR APPARATUS

(71) Applicant: Francis Ndeithi, Chandler, AZ (US)

(72) Inventor: Francis Ndeithi, Chandler, AZ (US)

(*) Notice: Subject to any disclaimer, the term of this patent is extended or adjusted under 35 U.S.C. 154(b) by 36 days.

(21) Appl. No.: 16/520,527

(22) Filed: Jul. 24, 2019

(65) Prior Publication Data

US 2021/0022618 A1 Jan. 28, 2021

(51) Int. Cl.
| | |
|---|---|
| *A61B 5/0205* | (2006.01) |
| *A61B 5/1455* | (2006.01) |
| *A61B 5/00* | (2006.01) |
| *A61B 5/022* | (2006.01) |
| *A61B 5/024* | (2006.01) |

(52) U.S. Cl.
CPC ........ *A61B 5/0205* (2013.01); *A61B 5/14551* (2013.01); *A61B 5/6826* (2013.01); *A61B 5/7445* (2013.01); *A61B 5/7475* (2013.01); *A61B 5/024* (2013.01); *A61B 5/02241* (2013.01); *A61B 2505/07* (2013.01); *A61B 2560/0214* (2013.01); *A61B 2562/046* (2013.01)

(58) Field of Classification Search
CPC ................ A61B 5/0205; A61B 5/7445; A61B 5/7475; A61B 5/14551; A61B 5/6826; A61B 2505/07; A61B 5/02241; A61B 2560/0214; A61B 5/024; A61B 2562/046
USPC ......................................................... 600/301
See application file for complete search history.

(56) References Cited

U.S. PATENT DOCUMENTS

| | | | |
|---|---|---|---|
| 5,792,052 A | 8/1998 | Isaacson | |
| 7,238,159 B2 | 7/2007 | Banet | |
| 8,417,309 B2 | 4/2013 | Price | |
| 8,727,977 B2 | 5/2014 | Banet | |
| D718,455 S | 11/2014 | Maser | |
| 9,596,999 B2 | 3/2017 | Moon | |
| 9,795,300 B2 | 10/2017 | Al-Ali | |
| 2004/0034293 A1 | 2/2004 | Kimball | |
| 2008/0275317 A1* | 11/2008 | Cho | A61B 5/02416 600/310 |
| 2013/0253334 A1* | 9/2013 | Al-Ali | A61B 5/02416 600/476 |

* cited by examiner

*Primary Examiner* — Amanda K Hulbert
*Assistant Examiner* — Philip C Edwards

(57) ABSTRACT

A finger blood monitor apparatus for easily measuring blood pressure, pulse, and oxygen saturation includes a cylindrical housing defining a housing cavity. A front end has a finger aperture extending through to the housing cavity and a battery compartment is coupled within the housing cavity adjacent a battery aperture. A control panel is coupled within the housing cavity and has a plurality of control buttons extending through the sidewall. A CPU is coupled within the housing cavity and is in operational communication with the control panel and the battery compartment. A plurality of sensors is coupled within the housing cavity to measure a user's pulse, blood pressure, and peripheral oxygen saturation and display the readings on a plurality of display screens coupled within the sidewall.

8 Claims, 6 Drawing Sheets

FINGER BLOOD MONITOR APPARATUS

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION (1) Field of the Invention (2) Description of Related Art Including Information Disclosed Under 37 CFR 1.97 and 1.98

The disclosure and prior art relates to home medical tools and more particularly pertains to a new home medical tool for easily measuring blood pressure, pulse, and oxygen saturation.

BRIEF SUMMARY OF THE INVENTION

An embodiment of the disclosure meets the needs presented above by generally comprising a cylindrical housing having a front end, a back end, and a sidewall extending therebetween defining a housing cavity. The front end has a finger aperture extending through to the housing cavity and the sidewall has a battery aperture extending through to the housing cavity. The housing is configured to receive a user's finger through the finger aperture. A battery compartment is coupled within the housing cavity adjacent the battery aperture and is configured to receive a plurality of batteries. A battery cover is selectively engageable with the battery aperture to seal and alternatively expose the battery compartment. A control panel is coupled within the housing cavity and has a plurality of control buttons extending through the sidewall. The control panel is in operational communication with the battery compartment. A CPU is coupled within the housing cavity and is in operational communication with the control panel and the battery compartment. A plurality of display screens is coupled within the sidewall and is in operational communication with the CPU, the control panel, and the battery compartment. A plurality of sensors is coupled within the sidewall within the housing cavity from adjacent the finger aperture to adjacent the CPU. The plurality of sensors is in operational communication with the CPU, the control panel, and the battery compartment. The plurality of sensors is configured to measure a user's pulse, blood pressure, and peripheral oxygen saturation.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
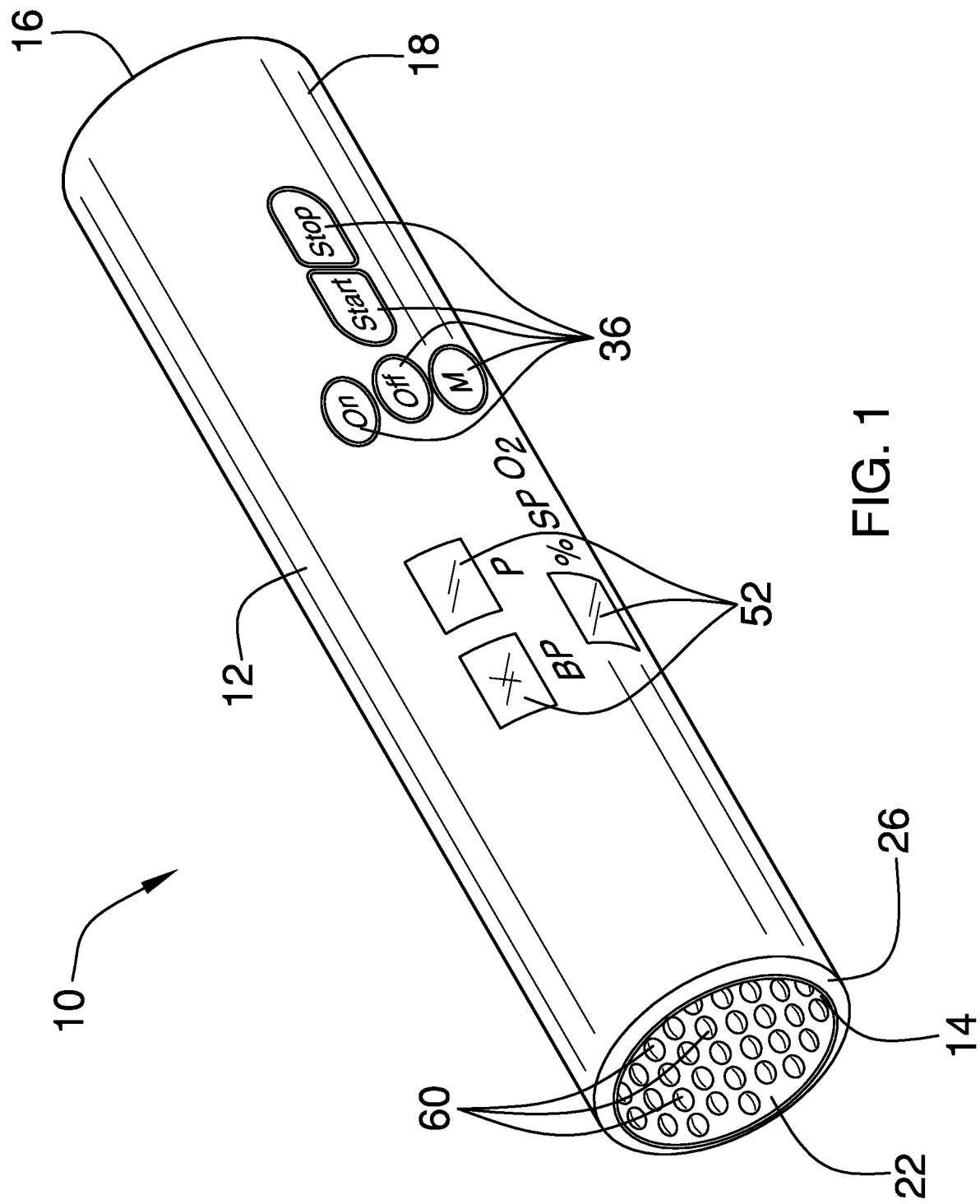
FIG. 1 is an isometric view of a finger blood monitor apparatus according to an embodiment of the disclosure.
Figure 2:
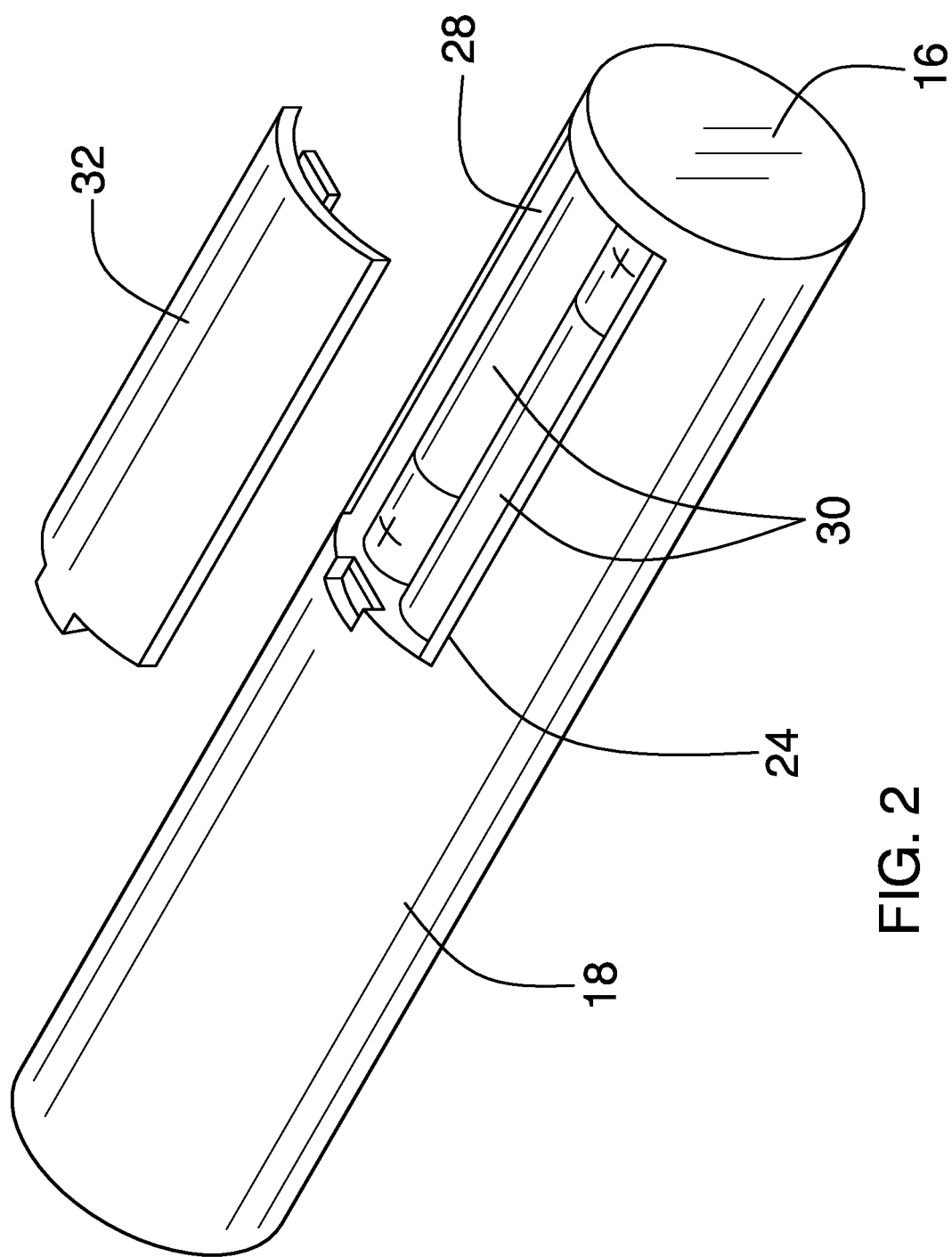
FIG. 2 is an isometric view of an embodiment of the disclosure.
Figure 3:
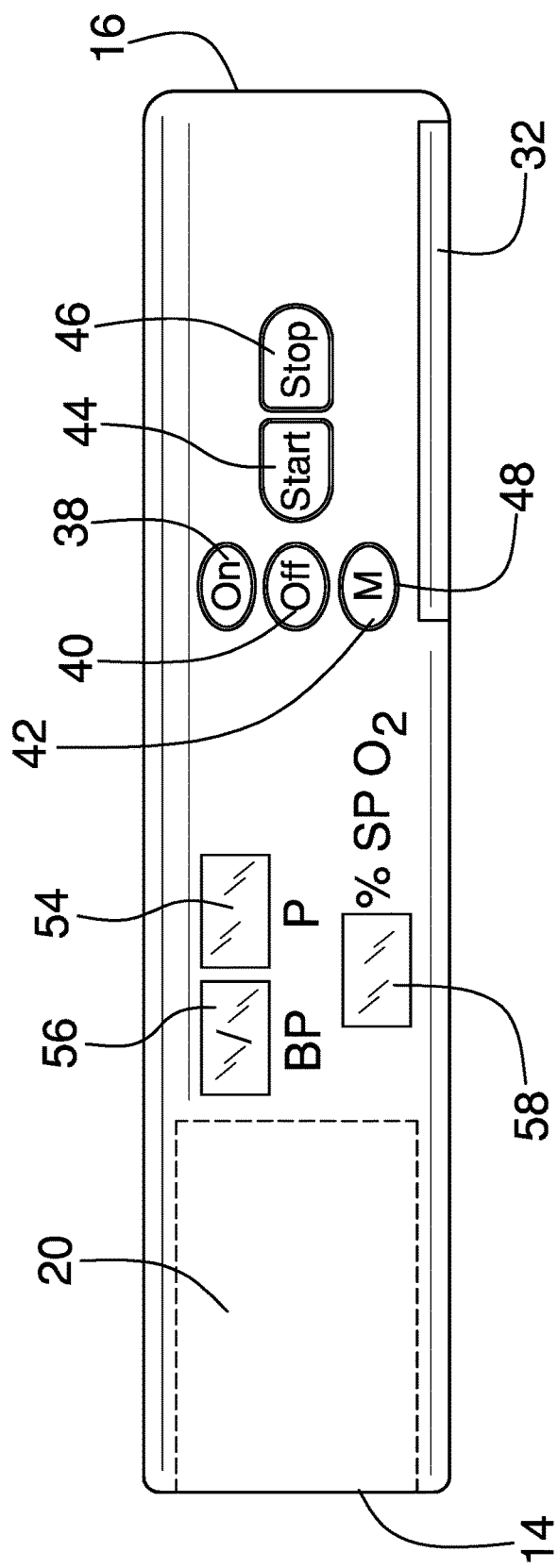
FIG. 3 is a front elevation view of an embodiment of the disclosure.
Figure 4:
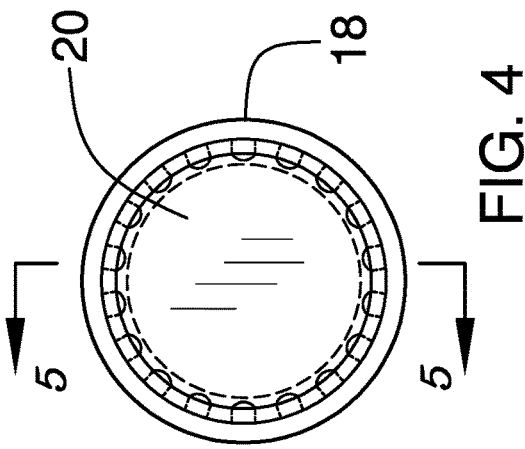
FIG. 4 is a side elevation of an embodiment of the disclosure.
Figure 5:
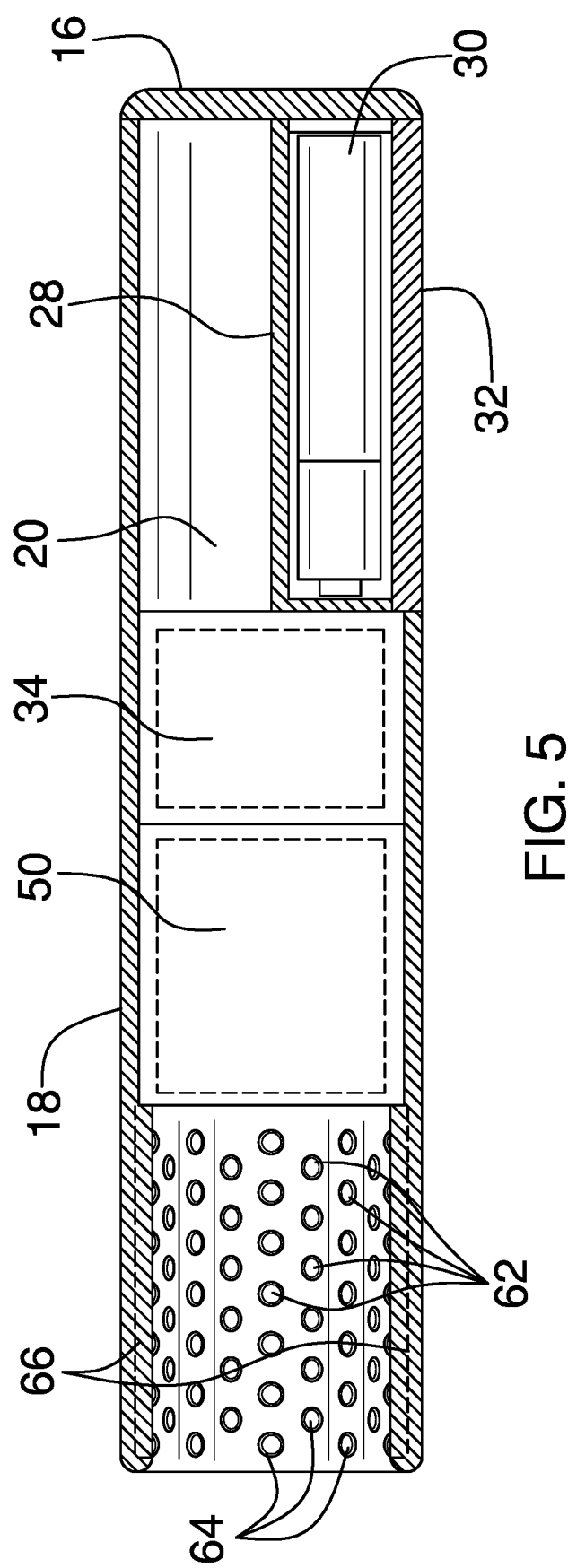
FIG. 5 is a cross-sectional view of an embodiment of the disclosure.
Figure 6:
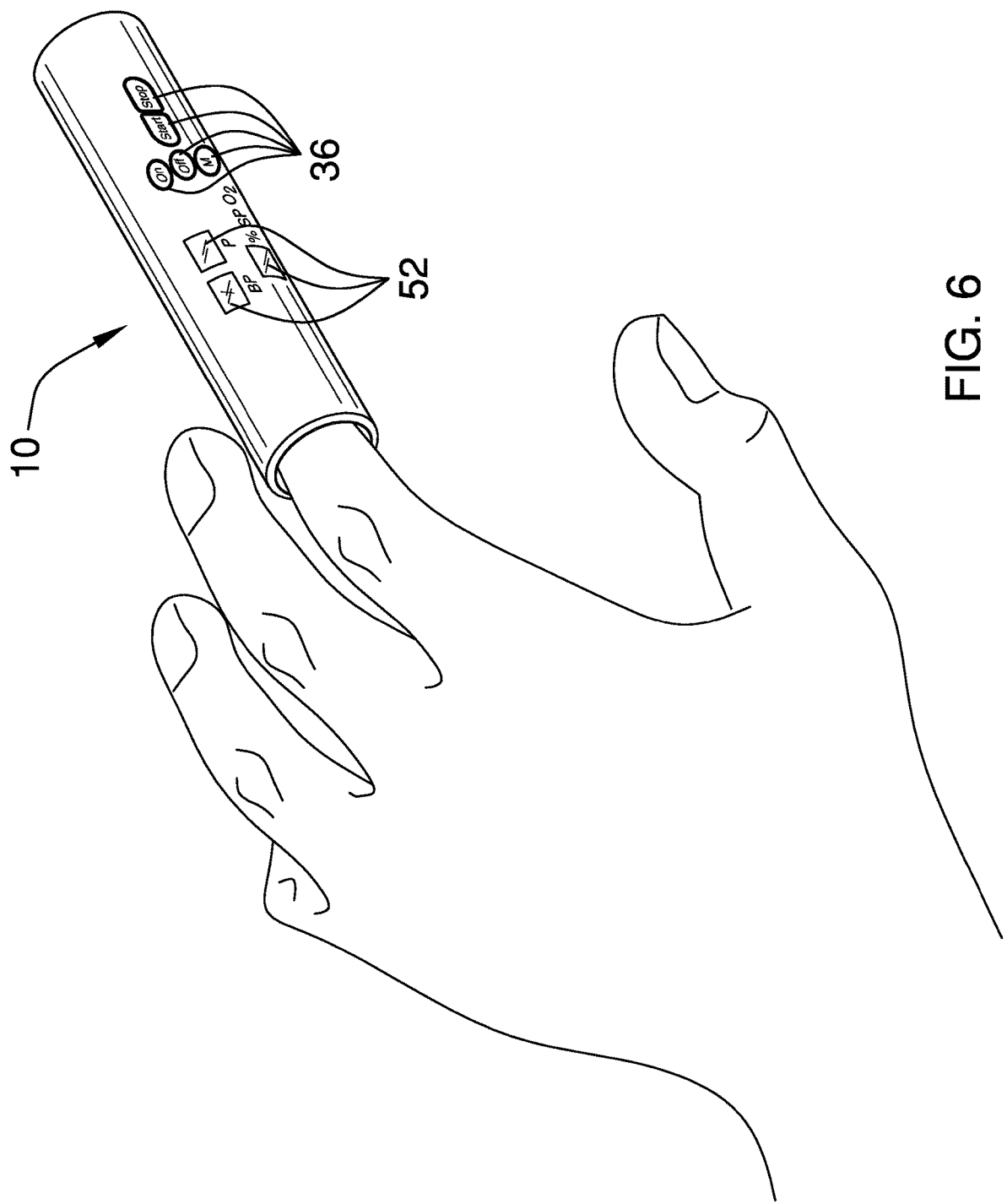
FIG. 6 is an in-use view of an embodiment of the disclosure.
Figure 7:
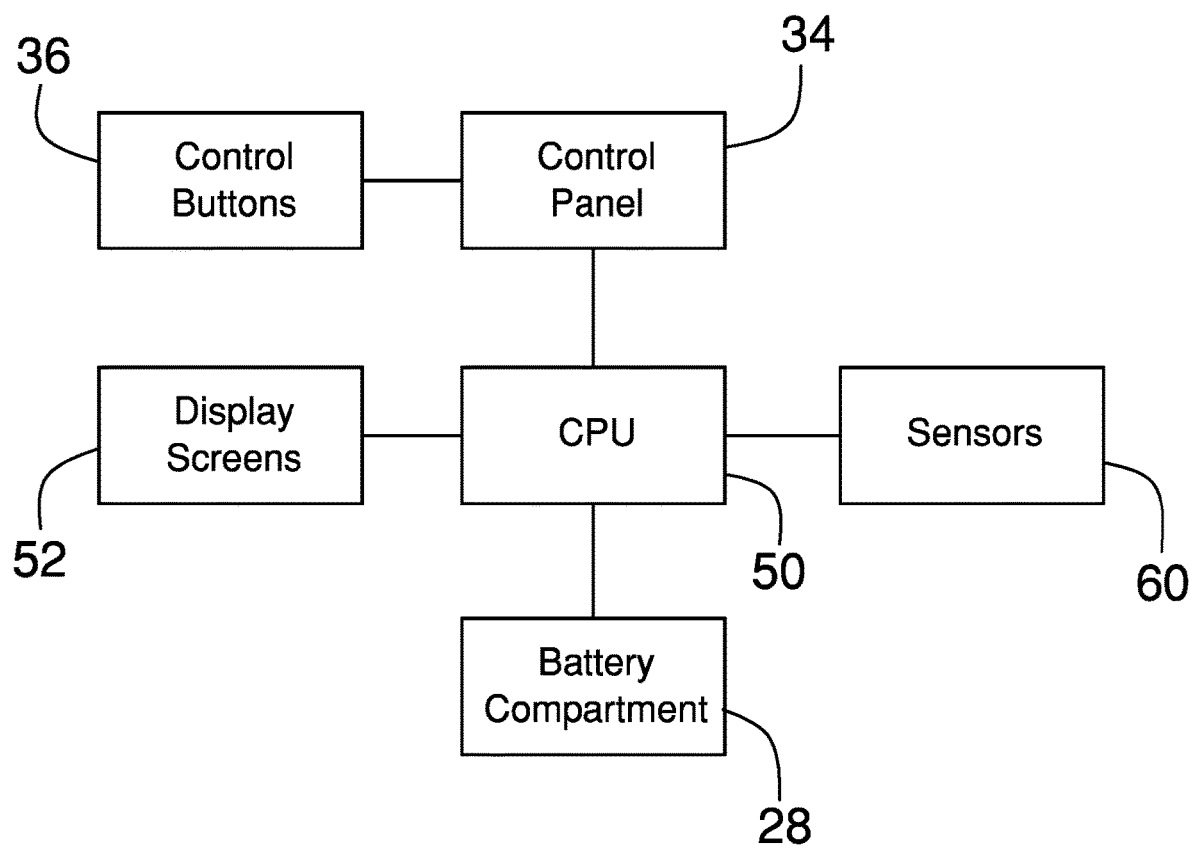
FIG. 7 is a block diagram of an embodiment of the disclosure.

With reference now to the drawings, and in particular to FIGS. 1 through 7 thereof, a new home medical tool embodying the principles and concepts of an embodiment of the disclosure and generally designated by the reference numeral 10 will be described.

As best illustrated in FIGS. 1 through 7, the finger blood monitor apparatus 10 generally comprises a cylindrical housing 12 cylindrical having a front end 14, a back end 16, and a sidewall 18 extending therebetween defining a housing cavity 20. The front end 14 has a finger aperture 22 extending through to the housing cavity 20. The sidewall 18 has a battery aperture 24 extending through to the housing cavity 20 proximal the back end 16. The sidewall 18 may have a chamfered edge 26 adjacent the finger aperture 22. The housing 12 is configured to receive a user's finger through the finger aperture 22 into the housing cavity 20.

A battery compartment 28 is coupled to the housing 12 within the housing cavity 20 adjacent the battery aperture 24. The battery compartment 28 is configured to receive a plurality of batteries 30. A battery cover 32 is selectively engageable with the battery aperture 24 to seal and alternatively expose the battery compartment 28. The battery cover 32 is rounded to conform to the sidewall 18 and maintain the cylindrical form of the apparatus 10. A control panel 34 is coupled within the housing cavity 20 adjacent the battery compartment 28 and has a plurality of control buttons 36 extending through the sidewall 18. The plurality of control buttons 36 comprises an on button 38, an off button 40, a mode button 42, a start button 44, and a stop button 46. The on button 38, the off button 40, and the mode button 42 are arranged in a vertical column 48. The start button 44 and the stop button 46 are adjacent and arranged to the right of the vertical column 48 aligned with the off button 40. The control panel 34 is in operational communication with the battery compartment 28. A CPU 50 is coupled within the housing cavity 20 adjacent the control panel 34 and is in operational communication with the control panel 34 and the battery compartment 28. A plurality of display screens 52 is coupled to the housing 12 and comprises a pulse screen 54, a blood pressure screen 56, and a peripheral oxygen saturation screen 58, denoted as "% SPO2". The blood pressure screen 56 and the pulse screen 54 are arranged side by side and the peripheral oxygen saturation screen 58 is arranged below the blood pressure screen 56 and the pulse screen 54. The plurality of display screens 52 is coupled within the sidewall 18 and is in operational communication with the CPU 50, the control panel 34, and the battery compartment 28.

A plurality of sensors 60 is coupled within the sidewall 18 within the housing cavity 20 from adjacent the finger aperture 22 to adjacent the CPU 50. The plurality of sensors 60 is in operational communication with the CPU 50, the control panel 34, and the battery compartment 28. The plurality of sensors 60 comprises a plurality of round optical sensors 62 disposed in a plurality of offset rows 64 around the sidewall 18 within the housing cavity 20. The plurality of optical sensors 62 comprises transmitters and photodetectors to perform transmissive pulse oximetry. An electronic sphygmomanometer 66 is coupled within the sidewall 18 around the plurality of optical sensors 62 to measure blood pressure and pulse.

In use, the user inserts her finger into the finger aperture 22 and uses the plurality of control buttons 36 to take the desired blood readings.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A finger blood monitor apparatus comprising:
   a housing, the housing being cylindrical and having a front end, a back end, and a sidewall extending therebetween defining a housing cavity, the front end having an integral finger aperture extending through to the housing cavity, the sidewall having a battery aperture extending through to the housing cavity, the housing being configured to receive a user's finger through the finger aperture;
   a battery compartment coupled to the housing, the battery compartment being coupled within the housing cavity adjacent the battery aperture, the battery compartment being configured to receive a plurality of batteries;
   a battery cover coupled to the housing, the battery cover being selectively engageable with the battery aperture to seal and alternatively expose the battery compartment;
   a control panel coupled to the housing, the control panel being coupled within the housing cavity and having a plurality of control buttons extending through the sidewall, the control panel being in operational communication with the battery compartment;
   a CPU coupled to the housing, the CPU being coupled within the housing cavity and being in operational communication with the control panel and the battery compartment;
   a plurality of display screens coupled to the housing, the plurality of display screens being coupled within the sidewall and being in operational communication with the CPU, the control panel, and the battery compartment; and
   a plurality of sensors coupled to the housing, the plurality of sensors being coupled within the sidewall within the housing cavity from adjacent the finger aperture to adjacent the CPU, the plurality of sensors being in operational communication with the CPU, the control panel, and the battery compartment, the plurality of sensors being configured to measure a user's pulse, blood pressure, and peripheral oxygen saturation.

2. The finger blood monitor apparatus of claim 1 further comprising the plurality of control buttons comprising an on button, an off button, a mode button, a start button, and a stop button.

3. The finger blood monitor apparatus of claim 2 further comprising the on button, the off button, and the mode button being arranged in a vertical column, the start button and the stop button being adjacent and arranged to the right of the vertical column aligned with the off button.

4. The finger blood monitor apparatus of claim 1 further comprising the plurality of display screens comprising a pulse screen, a blood pressure screen, and a peripheral oxygen saturation screen.

5. The finger blood monitor apparatus of claim 4 further comprising the blood pressure screen and the pulse screen being arranged side by side and the peripheral oxygen saturation screen being arranged below the blood pressure screen and the pulse screen.

6. The finger blood monitor apparatus of claim 1 further comprising the plurality of sensors comprising a plurality of round optical sensors disposed in a plurality of offset rows around the sidewall within the housing cavity, the plurality of optical sensors comprising transmitters and photodetectors to perform transmissive pulse oximetry, and an electronic sphygmomanometer coupled within the sidewall to measure blood pressure and pulse.

7. The finger blood monitor apparatus of claim 1 further comprising the sidewall having a chamfered edge adjacent the finger aperture.

8. A finger blood monitor apparatus comprising:
- a housing, the housing being cylindrical and having a front end, a back end, and a sidewall extending therebetween defining a housing cavity, the front end having an integral finger aperture extending through to the housing cavity, the sidewall having a battery aperture extending through to the housing cavity, the sidewall having a chamfered edge adjacent the finger aperture, the housing being configured to receive a user's finger through the finger aperture;
- a battery compartment coupled to the housing, the battery compartment being coupled within the housing cavity adjacent the battery aperture, the battery compartment being configured to receive a plurality of batteries;
- a battery cover coupled to the housing, the battery cover being selectively engageable with the battery aperture to seal and alternatively expose the battery compartment;
- a control panel coupled to the housing, the control panel being coupled within the housing cavity and having a plurality of control buttons extending through the sidewall, the plurality of control buttons comprising an on button, an off button, a mode button, a start button, and a stop button, the on button, the off button, and the mode button being arranged in a vertical column, the start button and the stop button being adjacent and arranged to the right of the vertical column aligned with the off button, the control panel being in operational communication with the battery compartment;
- a CPU coupled to the housing, the CPU being coupled within the housing cavity and being in operational communication with the control panel and the battery compartment;
- a plurality of display screens coupled to the housing, the plurality of display screens comprising a pulse screen, a blood pressure screen, and a peripheral oxygen saturation screen, the blood pressure screen and the pulse screen being arranged side by side and the peripheral oxygen saturation screen being arranged below the blood pressure screen and the pulse screen, the plurality of display screens being coupled within the sidewall and being in operational communication with the CPU, the control panel, and the battery compartment; and
- a plurality of sensors coupled to the housing, the plurality of sensors being coupled within the sidewall within the housing cavity from adjacent the finger aperture to adjacent the CPU, the plurality of sensors being in operational communication with the CPU, the control panel, and the battery compartment, the plurality of sensors being configured to measure a user's pulse, blood pressure, and peripheral oxygen saturation, the plurality of sensors comprising a plurality of round optical sensors disposed in a plurality of offset rows around the sidewall within the housing cavity, the plurality of optical sensors comprising transmitters and photodetectors to perform transmissive pulse oximetry, and an electronic sphygmomanometer coupled within the sidewall to measure blood pressure and pulse.

* * * * *